(12) United States Patent
Cobb et al.

(10) Patent No.: US 7,759,105 B2
(45) Date of Patent: *Jul. 20, 2010

(54) PROBIOTIC COMPOSITION USEFUL FOR DIETARY AUGMENTATION AND/OR COMBATING DISEASE STATES AND ADVERSE PHYSIOLOGICAL CONDITIONS

(75) Inventors: Mark L. Cobb, Dallas, TX (US); Alyson Cobb, Dallas, TX (US)

(73) Assignee: Cobb & Company, LLP, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/840,992

(22) Filed: Aug. 19, 2007

(65) Prior Publication Data

US 2007/0280910 A1  Dec. 6, 2007

(51) Int. Cl.
- C12N 1/12 (2006.01)
- A01N 63/00 (2006.01)
- C12N 1/20 (2006.01)
- A01N 65/00 (2009.01)
- A01N 25/00 (2006.01)

(52) U.S. Cl. .................. 435/252.1; 435/252.4; 435/822; 424/93.1; 424/93.3; 424/93.4; 424/93.44; 424/93.46; 424/93.462; 514/777

(58) Field of Classification Search .................. None
See application file for complete search history.

(56) References Cited

U.S. PATENT DOCUMENTS

| | | |
|---|---|---|
| 5,599,795 A | 2/1997 | McCann et al. |
| 6,203,797 B1 | 3/2001 | Perry |
| 6,207,703 B1 | 3/2001 | Ponikau |
| 6,254,910 B1 | 7/2001 | Paluch |
| 6,312,746 B2 | 11/2001 | Paluch |
| 6,399,114 B2* | 6/2002 | Foreman ............... 424/725 |
| 6,447,772 B1 | 9/2002 | Houston |
| 6,461,607 B1 | 10/2002 | Farmer |
| 6,471,999 B2 | 10/2002 | Couzy et al. |
| 6,551,633 B2 | 4/2003 | Couzy et al. |
| 6,746,671 B2 | 6/2004 | Steidler et al. |
| 6,811,786 B1 | 11/2004 | Farmer et al. |
| 6,861,053 B1 | 3/2005 | Lin et al. |
| 7,192,581 B2 | 3/2007 | Park et al. |
| 2002/0013270 A1 | 1/2002 | Bolte |
| 2002/0022019 A1 | 2/2002 | Laulund |
| 2003/0003107 A1* | 1/2003 | Farmer ............... 424/184.1 |
| 2003/0031659 A1 | 2/2003 | Farmer |
| 2003/0175305 A1 | 9/2003 | Garner et al. |
| 2004/0047896 A1 | 3/2004 | Malnoe et al. |
| 2004/0167062 A1 | 8/2004 | Bolte |
| 2005/0100535 A1* | 5/2005 | Farmer et al. ............ 424/93.46 |
| 2005/0100559 A1* | 5/2005 | Myatt et al. ............. 424/234.1 |
| 2005/0153018 A1 | 7/2005 | Ubbink et al. |
| 2006/0177424 A1 | 8/2006 | Cobb et al. |
| 2007/0071739 A1 | 3/2007 | Cobb et al. |
| 2007/0098744 A1 | 5/2007 | Knorr et al. |
| 2007/0128178 A1 | 6/2007 | Corthesy-Theulaz et al. |
| 2007/0141039 A1 | 6/2007 | Collins et al. |
| 2007/0280911 A1 | 12/2007 | Cobb et al. |
| 2007/0280912 A1 | 12/2007 | Cobb et al. |

FOREIGN PATENT DOCUMENTS

| | | | |
|---|---|---|---|
| EP | 0508701 A2 | * | 10/1992 |
| WO | WO 98/54982 | * | 12/1998 |
| WO | WO0193904 A1 | | 6/2001 |
| WO | WO 02/05829 A2 | * | 1/2002 |

OTHER PUBLICATIONS

ThreeLac® Study-Nine Month Results, copyright © 2005-2006 (http://www.autism-study.com/ retrieved online Jun. 12, 2008).*
Candida Support, copyright © 2002-2008 (http://candidasupport.org/ retrieved online Jun. 12, 2008).*
Vecchi et al. International Journal of Probiotics and Prebiotics vol. 1, No. 1, pp. 3-10, 2006.*
Bezkorovainy et al. American Journal of Clinical Nutrition, vol. 73, No. 2, 399S-405S, Feb. 2001.*
Trenev, Natasha. (Probiotics: Nature's Internal Healers. 1998. Avery Trade, New York) p. 129 and 132-233.*
Kim et al. Korean J Gastroenterol. Jun. 2006; 47 (6):413-419.*
Nutraceutical News Jul./Aug. 2007 (http://www.ifssolutions.com/news20070708.html) retrieved Jul. 20, 2009.*

(Continued)

*Primary Examiner*—Robert Mondesi
*Assistant Examiner*—Oluwatosin Ogunbiyi
(74) *Attorney, Agent, or Firm*—Steven J. Hultquist; Intellectual Property / Technology Law

(57) ABSTRACT

A probiotic composition including the bacilli (1) *Bacillus subtilis*, (2) *Bacillus coagulans*, and (3) *Enterococcus faecium*. The composition may further include a carrier medium, such as fructo-oligo-saccharides (FOS), as incorporated in a dose form such as a pill, capsule, powder or sachet. The compositions of the invention may be usefully employed as health or nutritional supplements, food additives, or therapeutic agents for combating a wide variety of physiological disorders, such as irritable bowel syndrome, autism, and fibromyalgia.

3 Claims, No Drawings

OTHER PUBLICATIONS

Product information for Symbion™ (http://www.symbionforlife.com) retrieved Jul. 20, 2009.*

Enterococcus faecium (scientific name)—synonym is Streptococcus faecium. (http://www.uniprot.org/taxonomy/1352) retrieved Jul. 20, 2009.*

Chou, Yen-Yi, et al., "Vancomycin-resistant enterococcal bacteremia: comparison of clinical features and outcome between Enterococcus faecium . . . ", "J. Microbiol. Immunol. Infect.", Apr. 2008, pp. 124-129, vol. 41.

"Global Health Trax Inc. website advertisment for Threelac product", "http://www.ghtdirect.com/threelac_main.aspx", 2007, Publisher: Global Health Trax Inc. website.

Tomkins, T. et , "A comprehensive review of post-market clinical studies performed in adults with an Asian probiotic formulation", "Beneficial Microbes", Article in Press, published online 2009, Publisher: Wageningen Academic Publishers.

, "How does candida harm my body?", "First found online at http://www.1stcandidacure.com/candidacureplan.html", Aug. 26, 2004 .

, "Chronic Fatigue, Fybromyalgia and other Autoimmune disease", "First found online at http://www.candidasupport.org/faq'sandingredie.html", Aug. 20, 2003.

, "Eliminate the underlying cause", "First found online at http://www.candidfree.net/pages/1/index.html", Sep. 21, 2004.

Edelson, Stephen M., "The candida yeast-autism connection", "First found online at http://www.autism.org/candida.html", Aug. 20, 2003.

Harrison, Robert , "Candida Research Article", "Found online at http://www.candidayeastinfection.com/researcharticle.html", Jul. 13, 2007.

, "Lactobacillus Sporogenes—Introduction to LactoSpore", "Found online at http://www.lactospore.com", 2000.

Lewis, Carol, "Irritable Bowel Syndrome: A poorly understood disorder", "FDA Consumer Magazine", Jul.-Aug. 2001, pp. 1-9, Publisher: U.S. Food and Drug Administration.

, "Primal Defense—Product Information", "First found online at http://www.forhealthsolutions.net/primal-defense.html", Aug. 20, 2003.

, "ThreeLac Candida Defense—How does Nature's Biotics help?", "First found online at http://www.gethealthyagain.com/candida", Aug. 20, 2003.

, "Benefits of Threelac", "http://www.ghtdirect.com/threelac_main.aspx", Aug. 14, 2007.

* cited by examiner

PROBIOTIC COMPOSITION USEFUL FOR DIETARY AUGMENTATION AND/OR COMBATING DISEASE STATES AND ADVERSE PHYSIOLOGICAL CONDITIONS

BACKGROUND OF THE INVENTION

The present invention relates to compositions and methods useful for dietary augmentation, to provide a probiotic supplement useful in a dietary regimen, and/or to provide therapeutic intervention for the treatment, prevention, amelioration and/or regulation of a variety of disease states and/or adverse physiological conditions.

DESCRIPTION OF THE RELATED ART

Candidiasis is a fungal infection of mucosal membranes and other tissues. The infection is caused by the yeast-like organism *Candida*. Numerous species of *Candida* exist, including *C. albicans*. The recent increase in candidiasis is most likely caused by the rising incidence of AIDS, more intensive regimens of cancer therapy, complications of abdominal or cardio-thoracic surgery, organ transplantations, burns and trauma. In addition, immunocompromised individuals and women of childbearing age, especially pregnant women or women with one or more childbirths, are known to be more susceptible to microbial pathogenesis. Alteration of the fungi microenvironment, including changes in pH, temperature, osmotic pressure, and hormonal concentrations, is currently considered to be accountable for the initiation of *C. albicans* infection symptoms.

Women can contract vaginal candidiasis by engaging in sexual activity with men who may not be aware they are carrying the infection because the symptoms are so mild in men that they are either overlooked or are completely unfelt.

It has recently come to light that candidiasis strikes immunocompetent individuals as well. For example, the widespread use of anti-microbial agents, such as broad spectrum antibiotics, has resulted in a number of serious clinical consequences. For example, antibiotics can kill beneficial, non-pathogenic microorganisms (i.e., flora) within the gastrointestinal tract, but are powerless against the yeasts in the GI tract. As a result, the gastrointestinal yeasts normally kept in check by the flora begin to grow at an excessive rate. In addition to antibiotics, the unrestrained usage of steroids, birth control pills, antacid and anti-ulcer medications, as well as diets high in sugar have been blamed for the rapid rise in candidiasis in the general population.

Common candidiasis symptoms include, but are not limited to, vaginal yeast infections, psoriasis and other dermatosis, fatigue or lethargy, depression, headaches, muscle aches, pain and/or swelling in the joints, constipation and/or diarrhea, bloating, sexual dysfunction, chronic hives, irritability, PMS, arthritis, muscle pain, memory loss, vaginitis, impotence, hypoglycemia, menstrual problems, urinary disorders, anxiety, insomnia, sensitivity to foods, thrush, and halitosis.

It is theorized that approximately 85% of Americans are or have been infected by some strain of yeast or fungus. Fungal infections can be systemic, subcutaneous, cutaneous or superficial (involving the outermost skin or hair).

Fungal infections are among the most difficult to effectively treat and regimens must be continued for months before results can be seen. Currently, there are several different types of drugs on the market that can provide effective therapy, as well as diets, such as the four step Candida diet. The Candida diet includes: the immediate elimination of antibiotics, birth control pills and other hormone-altering substances; a low-sugar, low-carbohydrate, high protein diet; the medical use of agents such as nystatin; and the strengthening of the immune system through supplementation. Though often effective, drugs and the Candida diet are cost prohibitive to many and more often than not, the symptoms return upon termination of the regimen.

To date, the cause of fibromyalgia syndrome, which causes people to feel chronic pain all over their bodies and suffer from symptoms such as sleep disturbances, fatigue and headaches, is unknown. It has been reported that an estimated four to six million Americans suffer from fibromyalgia, however presently there is no drug designed specifically to treat it.

Like fibromyalgia, the cause of autism continues to evade researchers. There are numerous theories put forth to explain the onset of autism in children including, but not limited to: an excess of opioid-like species whose effects on the brain produce the symptoms of autism; vaccinations, e.g., MMR; genetics; toxic environmental substances; and difficulties during pregnancy.

It would be beneficial to provide an affordable treatment that would prevent or inhibit the unchecked growth of fungus, including Candidiasis.

It would also be beneficial to provide a safe, effective and affordable therapeutic composition that is also effective to treat, prevent, ameliorate or regulate other disease states and adverse physiological conditions including, but not limited to, autism, delayed development, acid reflux disease, vaginal yeast infections, impaired hearing, chronic ear infections, seasonal allergies, Fibromyalgia syndrome, Crohn's disease, colitis, irritable bowel syndrome, interstitial cystitis, acne, sinusitis, rheumatoid arthritis, chronic fatigue syndrome, asthma, attention deficit disorder, attention deficit/hyperactivity disorder, rosacea, multiple sclerosis, hyperglycemia, Ménière's disease, Addison's disease, Parkinson's disease, Lou Gehrig's disease, ankylosing spondylitis, celiac disease, Graves' disease, Guillain-Barre' syndrome, Hashimoto's disease, lupus erythematosus, myasthenia gravis, Sjogren's syndrome, alopecia universalis, endometriosis, eczema, seborrheic dermatitis, jock itch, hives, athlete's foot, psoriasis, sarcoidosis, schizophrenia, scleroderma, ulcerative colitis and vulvodynia.

It would be further beneficial to provide effective augmentation of a diet of a subject with a probiotic supplement, particularly one that has correlative benefit in respect of one or more of the foregoing physiological conditions.

SUMMARY OF THE INVENTION

The present invention relates to compositions and methods useful for dietary augmentation, to provide a probiotic regimen, and/or to provide therapeutic intervention for the treatment, prevention, amelioration and/or regulation of disease states and/or other adverse physiological conditions, such as deleterious fungal overgrowth, Candidiasis, autism (including autism per se as well as milder variants such as Aspergers syndrome), delayed development, acid reflux disease, vaginal yeast infections, impaired hearing, chronic ear infections, seasonal allergies, Fibromyalgia syndrome, Crohn's disease, colitis, irritable bowel syndrome, interstitial cystitis, acne, sinusitis, rheumatoid arthritis, chronic fatigue syndrome, asthma, attention deficit disorder, attention deficit/hyperactivity disorder, rosacea, multiple sclerosis, hyperglycemia, Ménière's disease, Addison's disease, Parkinson's disease, Lou Gehrig's disease, ankylosing spondylitis, celiac disease, Graves' disease, Guillain-Barre' syndrome, Hashimoto's disease, lupus erythematosus, myasthenia gravis, Sjogren's syndrome, alopecia universalis, endometriosis, eczema, seborrheic dermatitis, jock itch, hives, athlete's foot, psoriasis, sarcoidosis, schizophrenia, scleroderma, ulcerative colitis and vulvodynia.

The invention in one aspect relates to a composition that is useful in such treatment applications, and that constitutes a useful health and nutritional supplement, in which the composition includes bacterial species (i) *Bacillus subtilis*, (ii) *Bacillus coagulans* and (iii) *Enterococcus faecium*.

These bacterial species may be in a dried form, e.g., lyophilized or sporolated form, in a suitable carrier medium, e.g., fructo-oligo-saccharide (FOS) medium, or other soluble fiber, sugar, nutrient or base material for the composition, with which the bacterial species can be presented in an orally administerable form.

In one specific aspect, the composition comprises (i) *Bacillus subtilis*, (ii) *Bacillus coagulans* and (iii) *Enterococcus faecium*, in a physiologically compatible carrier medium, wherein the ratio of *Bacillus subtilis:Bacillus coagulans: enterococcus faecium* is in a range of from 1:1.5:0.5 to 1:6:2.

In another specific aspect, the composition comprises the following bacterial components (i), (ii) and (iii):
(i) *Bacillus subtilis*, in an amount of 25 million to 1.5 billion colony forming units (CFUs)/1.5 gm dose
(ii) *Bacillus coagulans* in an amount of 50 million to 2 billion colony forming units (CFUs)/1.5 gm dose; and
(iii) *Enterococcus faecium* in an amount of 25 million to 1.5 billion colony forming units (CFUs)/1.5 gm dose, and a carrier medium, wherein a 1.5 gm dose contains from 5% to 75% of such bacterial components (i), (ii) and (iii), and from 25% to 95% of the carrier medium, wherein the CFU ratio of *Bacillus coagulans* to *Bacillus subtilis* is in a range of from 1 to 6, inclusive, and wherein the CFU ratio of *enterococcus faecium* to *Bacillus subtilis* is in a range of from 0.25 to 2, inclusive.

The composition in a further aspect includes a dose form comprising
(i) *Bacillus subtilis*, in an amount of 25 million to 1.5 billion colony forming units (CFUs);
(ii) *Bacillus coagulans* in an amount of 50 million to 2 billion colony forming units (CFUs); and
(iii) *Enterococcus faecium* in an amount of 25 million to 1.5 billion colony forming units (CFUs).

The composition in a still further aspect includes a dose form comprising
(i) *Bacillus subtilis*, in an amount of 100 million colony forming units (CFUs);
(ii) *Bacillus coagulans* in an amount of 200 million colony forming units (CFUs);
(iii) *Enterococcus faecium* in an amount of 100 million colony forming units (CFUs); and
(iv) fructo-oligo-saccharides (FOS) in an amount of from 500 to 1000 mg.

Such dose form in a further specific aspect includes the bacterial species in a non-microencapsulated form.

Such dose form in a still further aspect comprises a capsule containing the composition, wherein the capsule is devoid of any enteric coating.

Yet another aspect of the invention relates to a method of augmenting a diet of a subject with a probiotic supplement, comprising administration to the subject of a composition of the present invention.

The invention in another aspect relates to a method of treatment, prevention, amelioration and/or regulation of a physiological condition susceptible to therapeutic intervention by probiotic administration, comprising administering to a subject afflicted with or susceptible to such physiological condition and effective amount of the composition of the present invention.

The physiological condition related to such method in one aspect invention includes one or more of deleterious fungal overgrowth, Candidiasis, autism, delayed development, acid reflux disease, vaginal yeast infections, impaired hearing, chronic ear infections, seasonal allergies, Fibromyalgia syndrome, Crohn's disease, colitis, irritable bowel syndrome, interstitial cystitis, acne, sinusitis, rheumatoid arthritis, chronic fatigue syndrome, asthma, attention deficit disorder, attention deficit/hyperactivity disorder, rosacea, multiple sclerosis, hyperglycemia, Ménière's disease, Addison's disease, Parkinson's disease, Lou Gehrig's disease, ankylosing spondylitis, celiac disease, Graves' disease, Guillain-Barre' syndrome, Hashimoto's disease, lupus erythematosus, myasthenia gravis, Sjogren's syndrome, alopecia universalis, endometriosis, eczema, seborrheic dermatitis, jock itch, hives, athlete's foot, psoriasis, sarcoidosis, schizophrenia, scleroderma, ulcerative colitis and vulvodynia.

The invention in other aspects relates to a method of combating a disorder, e.g., autism or irritable bowel syndrome, in a subject, by administering to the subject an effective amount of a composition of the invention.

Other aspects, features and embodiments of the invention will be more fully apparent from the ensuing disclosure and appended claims.

DETAILED DESCRIPTION OF THE INVENTION

The present invention relates to probiotic compositions and methods useful for dietary augmentation, to provide a probiotic supplement useful in a dietary regimen, and/or to provide therapeutic intervention for the treatment, prevention, amelioration and/or regulation of a variety of disease states and/or adverse physiological conditions.

Applicants have discovered that the compositions of the present invention are unexpectedly efficacious as a dietary augmentation and a therapeutic intervention for combating a variety of disease states and adverse physiological conditions, including, but not limited to, fungal overgrowth, Candida, autism, delayed development, acid reflux disease, vaginal yeast infections, impaired hearing, chronic ear infections, seasonal allergies, Fibromyalgia syndrome, Crohn's disease, colitis, irritable bowel syndrome, interstitial cystitis, acne, sinusitis, rheumatoid arthritis, chronic fatigue syndrome, asthma, attention deficit disorder, attention deficit/hyperactivity disorder, rosacea, multiple sclerosis, hyperglycemia, Ménière's disease, Addison's disease, Parkinson's disease, Lou Gehrig's disease, ankylosing spondylitis, celiac disease, Graves' disease, Guillain-Barre' syndrome, Hashimoto's disease, lupus erythematosus, myasthenia gravis, Sjogren's syndrome, alopecia universalis, endometriosis, eczema, seborrheic dermatitis, jock itch, hives, athlete's foot, psoriasis, sarcoidosis, schizophrenia, scleroderma, ulcerative colitis and vulvodynia.

For example, applicants have surprisingly discovered that compositions of the present invention are able to effectively ameliorate the symptoms of fibromyalgia. Additionally, applicants have discovered that when autistic patients were administered the composition of the present invention, their manifested symptoms (i.e., minimal eye contact, verbal skills, etc.) were lessened in severity. In many cases, the symptoms of autism were no longer present and the diagnosis was removed. The term "effectively ameliorate" refers to substantial improvement in the symptoms associated with the subject disease state or physiological condition, e.g., at least 50% improvement in such symptoms.

The gastrointestinal microflora has been shown to play a number of vital roles in maintaining gastrointestinal tract function and overall physiological health. For example, the growth and metabolism of the many individual bacterial species inhabiting the gastrointestinal tract depend primarily upon the substrates available to them, most of which are derived from the diet. See e.g., Gibson G. R. et al., 1995. Gastroenterology 106: 975-982; Christi, S. U. et al., 1992. Gut 33: 1234-1238. These findings have led to attempts to modify the structure and metabolic activities of the community through diet, primarily with probiotics, which are live microbial food supplements. Probiotic microorganisms are live microorganisms that confer a benefit when administered in adequate amounts to confer a health benefit on the host, often by inhibiting the growth of other biological organisms in the same corporeal environment. The best known probiotics are the lactic acid-producing bacteria (i.e., Lactobacilli) and Bifidobacteria, which are widely utilized in yoghurts and other dairy products. These probiotic organisms are non-pathogenic and non-toxigenic, retain viability during storage, and survive passage through the stomach and small intestine. Since probiotics do not permanently colonize the host, they need to be ingested regularly for any health promoting properties to persist. Commercial probiotic preparations are generally comprised of mixtures of Lactobacilli and Bifidobacteria, although yeast such as Saccharomyces has also been utilized.

Probiotic microorganisms can be employed to protect the body against pathogens, maintain vital chemical and microflora balance in the gastrointestinal tract, produce essential vitamins and hormones, and assist in stimulating immune response.

The composition of the present invention includes the bacilli *Bacillus subtilis, Bacillus coagulans* and *Enterococcus faecium*, in combination with one another. The bacterial composition of the present invention, in various embodiments thereof, may comprise, consist of, or consist essentially of the combination of these three types of bacteria, and a physiologically compatible carrier medium for such bacteria.

*Bacillus coagulans* is a non-pathogenic, Gram positive, spore-forming bacteria that produces L(+) lactic acid (dextrorotatory) under homo-fermentation conditions. It has been isolated from natural sources, such as heat-treated soil samples inoculated into nutrient medium (see e.g., Bergey's Manual of Systemic Bacteriology, Vol. 2, Sneath, P. H. A. et al., eds., Williams & Wilkins, Baltimore, Md., 1986). *Bacillus coagulans* has also been utilized to produce lactic acid (U.S. Pat. No. 5,079,164). Though not naturally found in the gut, *Bacillus coagulans* strains have been used as general nutritional supplements and agents to control constipation and diarrhea in humans and other animals.

*Bacillus coagulans* strains and their growth requirements have been described previously (see e.g., Baker, D. et al, *Can. J. Microbiol.*, 6: 557-563, 1960; Nakamura, H. et al, *Int. J. Syst. Bacteriol.* 38: 63-73, 1988). In addition, various strains of *Bacillus coagulans* can be isolated from natural sources (e.g., heat-treated soil samples) using well-known procedures (see e.g., Bergey's Manual of Systemic Bacteriology, Vol. 2, p. 1117, Sneath, P. H. A. et al., eds., Williams & Wilkins, Baltimore, Md., 1986).

*Bacillus subtilis* is a Gram-positive, endospore-forming soil bacterium comprising aerobic and a few facultatively anaerobic rod-shaped bacteria. *Bacillus subtilis* was historically used to treat dysentery. It has been reported that ingested *Bacillus subtilis* are able to activate the human immune defense, including the IgM, IgG and IgA antibodies. *Bacillus subtilis* strains and their growth requirements are well known in the art.

*Enterococcus faecium* is a facultative anaerobic, Gram positive, cocci that produces L(+) lactic acid. The *Enterococcus faecium* strain is a natural inhabitant of the mammalian G.I. tract and causes many of the same problems as other members of the intestinal flora, including opportunistic urinary tract infections and wound infections.

The compositions of the invention, comprising the bacilli (A) *Bacillus subtilis*, (B) *Enterococcus faecium*, and (C) *Bacillus coagulans*, are suitably administered for dietary augmentation, to provide a probiotic supplement useful in a dietary regimen, and/or to provide therapeutic intervention for combating a variety of disease states and/or adverse physiological conditions, to effectively ameliorate symptoms thereof.

The respective bacterial species may be in a dried form, e.g., lyophilized or sporolated form, in a suitable carrier medium, e.g., fructo-oligo-saccharide (FOS) medium, or other soluble fiber, sugar, nutrient or base material for the composition, with which the bacterial species can be presented in an orally administerable form.

The compositions of the invention are usefully employed as probiotic supplements, food additives, food supplements, and compositions for combating a variety of disorders, such as deleterious fungal overgrowth, Candidiasis, autism, delayed development, acid reflux disease, vaginal yeast infections, impaired hearing, chronic ear infections, seasonal allergies, Fibromyalgia syndrome, Crohn's disease, colitis, irritable bowel syndrome, interstitial cystitis, acne, sinusitis, rheumatoid arthritis, chronic fatigue syndrome, asthma, attention deficit disorder, attention deficit/hyperactivity disorder, rosacea, multiple sclerosis, hyperglycemia, Ménière's disease, Addison's disease, Parkinson's disease, Lou Gehrig's disease, ankylosing spondylitis, celiac disease, Graves' disease, Guillain-Barre' syndrome, Hashimoto's disease, lupus erythematosus, myasthenia gravis, Sjogren's syndrome, alopecia universalis, endometriosis, eczema, seborrheic dermatitis, jock itch, hives, athlete's foot, psoriasis, sarcoidosis, schizophrenia, scleroderma, ulcerative colitis and vulvodynia, as well as other disorders that can be treated or prevented by probiotics, e.g., gastrointestinal disorders.

In the compositions of the invention, the bacilli *Bacillus subtilis, Bacillus coagulans* and *Enterococcus faecium* can be varied in relative therapeutic amounts with respect to one another. For example, in various specific embodiments, the ratio of *Bacillus subtilis:Bacillus coagulans:Enterococcus faecium* can be in a range of from 1:0.5:0.5 to 1:8:4. In other embodiments, each of the bacterial species is present in an amount of at least 25 million colony forming units (CFUs), e.g., a composition containing 25 million CFUs *Bacillus subtilis*, 200 million CFUs *Bacillus coagulans* and 25 million CFUs *Enterococcus faecium*.

In one specific aspect, the composition comprises (i) *Bacillus subtilis*, (ii) *Bacillus coagulans* and (iii) *Enterococcus faecium*, in a physiologically compatible carrier medium, wherein the ratio of *Bacillus subtilis:Bacillus coagulans: enterococcus faecium* is in a range of from 1:1.5:0.5 to 1:6:2.

The physiologically compatible carrier medium with which the bacterial species are employed, can be of any simple type, e.g., a pharmaceutically acceptable carrier such as fructo-oligo-saccharide (FOS) medium, or other soluble fiber, sugar, nutrient or base material for the composition, with which the bacterial species can be formulated, e.g., in an orally administerable form. Other carrier media include mannitol, insulin (a polysaccharide), polydextrose, arabinogalactan, polyolslactulose, lactitol, etc. A wide variety of materials can be used as carrier material in the practice of the present invention, as will be apparent to those of ordinary skill in yard, based on the disclosure herein.

The carrier medium, when present, can be blended with the bacterial species *Bacillus subtilis, Bacillus coagulans* and *Enterococcus faecium* in any suitable amounts, such as an amount of from 5% to 95% by weight of carrier medium, based on the total weight of the three bacterial species and the carrier medium, in various embodiments.

In other embodiments, the amount of carrier medium may be in a range having a lower limit of any of 5%, 10%, 12%, 15%, 20%, 25%, 28%, 30%, 40%, 50%, 60%, 70% or 75%, and an upper limit, higher than the lower limit, of any of 20%, 22%, 25%, 28%, 30%, 40%, 50%, 60%, 70%, 75%, 80%, 85%, 90%, and 95%.

The amount of carrier medium in a specific embodiment may be determined based on considerations of the specific dose form, relative amounts of the three bacterial species, the total weight of the composition including the carrier medium and the bacterial species, and the physical and chemical properties of the carrier medium, and other factors, as known to those of ordinary skill in the probiotic formulation art.

In various specific embodiments, the composition comprises:
(i) *Bacillus subtilis*, in an amount of 25 million to 1.5 billion colony forming units (CFUs)/1.5 gm dose
(ii) *Bacillus coagulans* in an amount of 50 million to 2 billion colony forming units (CFUs)/1.5 gm dose; and
(iii) *Enterococcus faecium* in an amount of 25 million to 1.5 billion colony forming units (CFUs)/1.5 gm dose, and a carrier medium.

Such 1.5 gm dose can for example contain from 5% to 75% of such bacterial components (i), (ii) and (iii), and from 25% to 95% of the carrier medium. It will be recognized that such 1.5 gm dose has been set forth above as one illustrative dosage of the composition of the invention, with respect to which the amounts of the various components of the composition have been specified.

In other embodiments of the invention, compositions are provided wherein the CFU ratio of *Bacillus coagulans* to *Bacillus subtilis* is in a range of from 1 to 6, inclusive, and wherein the CFU ratio of *enterococcus faecium* to *Bacillus subtilis* is in a range of from 0.25 to 2, inclusive.

The composition in a further embodiment includes a dose form comprising
(i) *Bacillus subtilis*, in an amount of 25 million to 1.5 billion colony forming units (CFUs);
(ii) *Bacillus coagulans* in an amount of 50 million to 2 billion colony forming units (CFUs); and
(iii) *Enterococcus faecium* in an amount of 25 million to 1.5 billion colony forming units (CFUs).

The composition in another embodiment constitutes a dose form comprising
(i) *Bacillus subtilis*, in an amount of 100 million colony forming units (CFUs);
(ii) *Bacillus coagulans* in an amount of 200 million colony forming units (CFUs);
(iii) *Enterococcus faecium* in an amount of 100 million colony forming units (CFUs); and
(iv) fructo-oligo-saccharides (FOS) in an amount of from 500 to 1000 mg.

The compositions of the invention, including the bacterial species and optionally a suitable carrier medium, can be provided in any suitable dose form for administration. The dose form is preferably a pill, powder, capsule, sachet, or the like, formulated for oral administration.

One preferred embodiment of the dose form is a capsule containing the composition of the invention including the three bacterial species in a dried form, blended with FOS. The composition may for example be constituted by 100 million CFUs of *Bacillus subtilis,* 200 million CFUs of *Bacillus coagulans*, and 100 million CFUs of *enterococcus faecium*, with 660 mg of FOS in a 750 mg capsule.

The capsule for such dose form can be of any suitable type, e.g., a gelatin capsule of a conventional variety. Preferably, such capsule is devoid of any enteric coating. Preferably the bacterial species are non-microencapsulated in the dose form.

The invention in a further embodiment relates to a method of augmenting a diet of a subject with a probiotic supplement, comprising administration to a subject of a composition of the present invention.

The invention in another aspect relates to a method of treatment, prevention, amelioration and/or regulation of a physiological condition susceptible to therapeutic intervention by probiotic administration, in which the method includes administering to a subject afflicted with or susceptible to such physiological condition, an effective amount of the composition of the present invention.

The physiological condition related to such method in one aspect invention includes one or more of deleterious fungal overgrowth, Candidiasis, autism, delayed development, acid reflux disease, vaginal yeast infections, impaired hearing, chronic ear infections, seasonal allergies, Fibromyalgia syndrome, Crohn's disease, colitis, irritable bowel syndrome, interstitial cystitis, acne, sinusitis, rheumatoid arthritis, chronic fatigue syndrome, asthma, attention deficit disorder, attention deficit/hyperactivity disorder, rosacea, multiple sclerosis, hyperglycemia, Ménière's disease, Addison's disease, Parkinson's disease, Lou Gehrig's disease, ankylosing spondylitis, celiac disease, Graves' disease, Guillain-Barre' syndrome, Hashimoto's disease, lupus erythematosus, myasthenia gravis, Sjogren's syndrome, alopecia universalis, endometriosis, eczema, seborrheic dermatitis, jock itch, hives, athlete's foot, psoriasis, sarcoidosis, schizophrenia, scleroderma, ulcerative colitis and vulvodynia.

The composition of the invention has proven dramatically effective in ameliorating symptoms of autism, as shown by the empirical results of the examples set out hereinafter. Such composition has advantage in treating a pregnant mother and/or her subsequently delivered child, as a therapeutic intervention for preventing autism from developing in the child. The use of the composition of the invention for the treatment or prophylaxis of autism also includes such usage for lesser related disease states such as Asperger's syndrome.

An additional disease state for which the composition of the invention has demonstrated particular efficacy in ameliorating symptoms, as also shown by the ensuing data and examples, is irritable bowel syndrome.

It will be appreciated that the composition of the invention can be usefully employed for combating a variety of adverse physiological conditions for which probiotic treatment is advantageous. It will be further appreciated that the probiotic composition of the invention can be usefully employed as a food additive in foodstuffs of widely varied types, to realize the health, dietary and nutritional benefits of such composition.

The dosing regimen involving compositions in accordance with the present invention can be varied to achieve a desired result, such as may be determined empirically for a given individual subject, or by extrapolation from data obtained from administering the composition to a clinical or other test population. For example, the dosage regimen may be carried out to administer each of the three bacilli *Bacillus subtilis,*

Bacillus coagulans and Enterococcus faecium, in an amount that is within a range of from 40 million CFUs up to 2 billion CFUs per day for each of such bacilli, and wherein the relative amounts of each may be the same as or different from the others, each being independently selected from such range. The dose forms may be constituted as necessary for a specific dosing regimen, and such regimen may maintained or varied as appropriate to the desired result.

In general, the composition of the invention may be administered in any suitable dose amount that is effective as a health supplement, food supplement, food additive, and/or therapeutic agent to prevent, ameliorate, regulate, cure or otherwise treat a disease state or physiological condition in a subject in need of such intervention. As used herein, the phrase "effective amount" means an amount including at least 10 million CFUs of *Bacillus subtilis*, at least 100 million CFUs of *Bacillus coagulans* and at least 10 million CFUs of *Enterococcus faecium*.

In various specific embodiments, an effective dose of a composition of the present invention can be in a range of from 1.0 gm to 15.0 gm for an adult patient, more preferably between about 2.0 gm and about 10.0 gm of the composition. Effective doses can be administered to a subject at any suitable frequency, e.g., at least once a week, preferably once a day. Pediatric dosages may be in the range of 15% to 90% of adult dosages.

In therapeutic applications for combating an adverse physiological condition, a constant dosage of the composition can be administered over time, for example about 2 gm to about 4 gm per day, up to about 6 g to about 10 g per day, depending on the severity of the physiological condition. Once the physiological condition has been effectively ameliorated, the subject can in many instances decrease the dosage to about 2 gm to about 4 gm per day for maintenance purposes.

The desired dose may be presented in multiple (e.g., two, three, four, five, six, or more) sub-doses administered at appropriate intervals throughout the day.

The compositions of the invention may additionally and optionally include any suitable adjuvants, excipients, additives, carriers, additional therapeutic agents, bioavailability enhancers, side-effect suppressing components, diluents, buffers, flavoring agents, binders, preservatives or other ingredients that do not preclude the efficacy of the composition. In various preferred embodiments, the bacilli (*Bacillus subtilis, Enterococcus faecium*, and *Bacillus coagulans*) comprise from about 50% to about 90% by weight of the composition, based on the total weight of the composition including a carrier medium, most preferably from about 60% to about 80% by weight of the composition. It is generally preferred that the composition contain only the bacilli and a carrier medium, in a gelatin capsule that is devoid of any enteric coating, with the bacteria being in a dried form such as powder or granules, and the carrier medium likewise being in a dry powder or particulate form.

The compositions of the present invention are preferably formulated for oral administration. Other routes of administration can be employed, however, including, but not limited to, subcutaneous, intramuscular, intradermal, transdermal, intraocular, intraperitoneal, mucosal, vaginal, rectal, and intravenous. For example, a dose of the composition of the present invention can be presented in a gelatin capsule and inserted vaginally to treat vaginal yeast infections.

In one embodiment, the therapeutic composition of the invention may comprise at least 40 million CFUs of each of *Bacillus subtilis, Bacillus coagulans* and *Enterococcus faecium*, as contained in capsules containing from 25 to 200 milligrams of the mixture *Bacillus subtilis, Bacillus coagulans* and *Enterococcus faecium* with one or more excipients, such as 500-1,000 milligrams of fructo-oligosaccharides, in a unitary dose form tablet or capsule.

The compositions of the invention are readily manufactured. The respective bacterial species *Bacillus subtilis, Bacillus coagulans* and *Enterococcus faecium* are seeded from standard stock into a reactor and grown in standardized media until a predetermined CFU/gm concentration is reached. The bulk material then is drained from the reactor and dried by spray drying, lyophilization, or flatbed oven drying. The dried bacterial raw material then is blended with the carrier medium and the resulting mixture can be pressed into tablets, filled into foil pouches as a granular solid, or introduced into gelatin capsules as a particulate material.

The bacterial species therefore are present in the dose form as live bacteria, whether in dried, lyophilized, or sporolated form. *Bacillus coagulans* may for example be in a sporolated form, while *Enterococcus faecium* may not be in a sporolated form.

The features and advantages of the invention are more fully shown by the following illustrative and non-limiting examples.

In each of the following examples, the human test subject received a composition of the invention (referred to in the examples as "Composition A"), containing 10 wt. % of a bacterial mixture consisting of 25 million CFUs of *Bacillus subtilis*, 200 million CFUs of *Bacillus coagulans* and 25 million CFUs of *Enterococcus faecium*, and 90 wt. % of fructo-oligosaccharides (FOS). The composition in each of the examples was orally administered in the weight amount as specified in each such example.

EXAMPLE 1

A seven-and-a-half year-old male patient with autism for at least four years had substantial difficulties learning to speak, read, write and process language. The patient was orally administered approximately 4 g of Composition A per day with water. Within three weeks with such daily treatment, the patient learned to ride a two-wheel bicycle for the first time. After six weeks of such daily treatment, the patient's speech and his ability to read, write and process language improved substantially and his self-stimulating behaviors decreased.

EXAMPLE 2

A six year-old female patient with autism who had ceased verbalizing with her family, was orally administered approximately 2 g of Composition A per day with water. Within a few days, with daily administration, she started speaking again. Following four months of such daily administration, her verbal improvement leveled off, at which point the dosage was increased to approximately 4 g of Composition A per day with water.

EXAMPLE 3

A six year-old female patient with autism was orally administered approximately 0.5 g of Composition A per day with water. Following daily administration of the composition for four days, the patient experienced some constipation, which was treated. The patient displayed a large improvement in eye contact and verbal skills. Four weeks later, with daily administration of Composition A continued, the patient continued to show improvement.

EXAMPLE 4

A five year-old male patient with autism and a leaky gut was orally administered approximately 2 g of Composition A per day with water. The patient's gut began to heal immediately with a concomitant jump in verbal articulation. In addition, the patient's gluten infractions did not manifest themselves as they previously typically had done.

EXAMPLE 5

A three year-old male patient with autism was orally administered approximately 2 g of Composition A per day with water. The dosage was increased up to approximately 4 g of Composition A per day and is presently maintained at approximately 2 g of Composition A per day. Immediately, the patient began making better eye contact with others and responded to verbal requests from his mother. At the age of four, the diagnosis of autism was completely removed and the patient has entered traditional schools.

EXAMPLE 6

A three-and-a-half year-old female patient with autism and redness and itching associated with the autism was orally administered approximately 2 g of Composition A per day with water. The patient began repeating sounds and words, and responded to verbal requests from her parents. In addition, the redness and itching subsided and the patient was successfully potty trained for the first time without complaint.

EXAMPLE 7

A six-and-a-half year-old male patient with autism for at least four years was orally administered approximately 2 g of Composition A per day with water at age 5.5 years. Following thirty days of approximately 2 g/day of Composition A, the dosage was increased to approximately 4-6 g/day of the composition for the next thirty days. Thereafter, the dosage was reduced back to approximately 2 g/day of the composition for maintenance. The patient is no longer diagnosed as learning disabled and he is able to attend traditional schools.

EXAMPLE 8

A four year-old male patient with autism was orally administered approximately 2 g of Composition A per day with water. The dosage was increased up to approximately 4 g of the composition per day. At the age of five, the diagnosis of autism was completely removed and the patient has entered traditional schools.

EXAMPLE 9

A 48 year-old female patient with fibromyalgia who did massage therapy, yoga and Pilates, but failed to be relieved of the pain, was orally administered approximately 2 g of Composition A per day with water for two months. The patient's energy level increased substantially and she was able to play eighteen holes of golf on four consecutive days, was able to ride a bicycle sixteen miles and take several 5-6 mile hikes all within the same week, without exhaustion or extreme pain.

EXAMPLE 10

A 26 year-old female patient with fibromyalgia was orally administered approximately 2 g of Composition A per day with water. Within just four days, the patient noticed a substantial improvement, whereby the pain associated with the condition decreased and her night sweats disappeared.

EXAMPLE 11

A 55 year-old female patient with fibromyalgia and allergies was orally administered approximately 6 g of Composition A per day with water for about five months. She noticed a significant improvement of her fibromyalgia symptoms and a decrease in the severity of her allergies.

EXAMPLE 12

A 34 year-old female patient who had suffered fibromyalgia for at least five years was orally administered approximately 4 g of Composition A per day with water. Within three weeks of taking the composition, the patient experienced enough relief of her symptoms to stop taking sleeping pills and pain medications.

EXAMPLE 13

A 49 year-old female patient with fibromyalgia was orally administered approximately 6 g of Composition A per day with water. Her fibromyalgia is now in a reversed state, whereby her tender points are non-existent and she was able to exercise twenty five to forty five minutes per day.

EXAMPLE 14

An approximately twenty-five year-old female patient with a severe sinus infection and acid reflux was orally administered approximately 2 g of Composition A per day with water. Both the sinus infection and the acid reflux were completely stopped.

EXAMPLE 15

A 47 year-old female patient with acid reflux was orally administered approximately 2 g of Composition A per day with water for five days and then the dosage was increased to approximately 4 g of Composition A per day for the next ten days. The heartburn caused by the acid reflux improved and other indications, such as hot flashes and sores on her head, ceased.

EXAMPLE 16

A 58 year-old female patient with hearing problems and some tinnitus was orally administered approximately 2 g of Composition A per day with water. After experiencing some bowel pains, she increased the dosage of Composition A to approximately 4 g per day and started feeling much better. She regained almost all of the hearing in her right ear and the ringing in her ears subsided.

EXAMPLE 17

A 51 year-old female patient with hearing problems, irritable bowel syndrome, and high blood sugar was orally administered approximately 2 g of Composition A per day with water. She noticed an improvement in her irritable bowel symptoms and her blood sugar problems became more regulated, whereby she didn't become faint and panicky if she was unable to eat at the same time every day. In addition, although she still needed to wear two digital hearing aids, she noticed an improvement in her hearing whereby she began to hear noises, e.g., alarm clocks that were previously unheard.

EXAMPLE 18

A 36 year-old female patient with irritable bowel syndrome, tinnitus and depression was orally administered approximately 2 g of Composition A per day with water for three months. She noticed a significant improvement in her irritable bowel symptoms and discontinued her anti-depression medications. In addition, the noise in her ears ceased.

EXAMPLE 19

A 50 year-old female patient with adult onset asthma and allergies was orally administered approximately 2 g of Composition A per day with water for several weeks. Her asthma went away completely and she experienced considerable relief from her allergies.

EXAMPLE 20

A 37 year-old female patient with candidiasis and seasonal hayfever was orally administered approximately 2 g of Composition A per day with water for six months. For the first time in twenty years, the patient did not suffer from seasonal hayfever.

EXAMPLE 21

A 38 year-old female patient with chronic ear infections and hearing fluctuations over more than twenty years was orally administered approximately 2 g of Composition A per day with water. She experienced relief from her recurrent ear infections and her hearing improved.

EXAMPLE 22

A 33 year-old female patient with a persistent vaginal yeast infection vaginally administered a gelatin capsule containing approximately 2 g of Composition A. After several administrations, the yeast infection went away.

EXAMPLE 23

A 24 year-old female patient with a persistent vaginal itch vaginally administered two gelatin capsules containing approximately 4 g of Composition A. Immediately, the itching subsided.

EXAMPLE 24

A 52 year-old female patient with Type I diabetes was orally administered approximately 6 g of Composition A per day with water. She noticed that she was feeling more energetic and that her blood sugars had stabilized.

EXAMPLE 25

A 55 year-old female patient with Multiple Sclerosis was orally administered approximately 4 g of Composition A per day with water for sixteen days. Prior to taking the composition, the patient could not walk properly and she experienced tingling and numbness on her right side and pressure in her head. After just one day, the pressure in her head eased and the leg muscles spasms became less painful. She began to use her right hand to carry objects without dropping them. She could also walk around the house without help and did not tire as easily.

EXAMPLE 26

A questionnaire was provided to 500 individual users of Composition A. The questionnaire inquired about the disease state or physiological condition afflicting the individual, their gender, how much of the composition they took, how long they had been taking the composition, and their self-determined percent improvement. A total of 319 individuals responded. The results are tabulated in Table 1.

TABLE 1

| Disease State/ Adverse Physiological Condition | # of Respondents (Male or Female) | Dosage Administered/ day | Percent Improvement |
| --- | --- | --- | --- |
| autism | 4 M | ≈2 g to ≈6 g | 1 (less than 50%) |
|  |  |  | 3 (90%-100%) |
| delayed development | 1 F; 1 M | ≈4 g | 1 (less than 50%) |
|  |  |  | 1 (90%-100%) |
| acid reflux | 15 F; 1 M | ≈2 g to ≈8 g | 2 (less than 50%) |
|  |  |  | 1 (50%-60%) |
|  |  |  | 8 (70%-80%) |
|  |  |  | 5 (90%-100%) |
| impaired hearing | 6 F; 3 M | ≈2 g to ≈6 g | 1 (less than 50%) |
|  |  |  | 3 (70%-80%) |
|  |  |  | 5 (90%-100%) |
| chronic ear infections | 17 F; 1 M | ≈2 g to ≈8 g | 1 (less than 50%) |
|  |  |  | 4 (50%-60%) |
|  |  |  | 5 (70%-80%) |
|  |  |  | 8 (90%-100%) |
| seasonal allergies | 30 F; 5 M | ≈2 g to ≈10 g | 4 (less than 50%) |
|  |  |  | 6 (50%-60%) |
|  |  |  | 10 (70%-80%) |
|  |  |  | 15 (90%-100%) |
| fibromyalgia | 33 F; 3 M | ≈2 g to ≈10 g | 12 (less than 50%) |
|  |  |  | 5 (50%-60%) |
|  |  |  | 10 (70%-80%) |
|  |  |  | 9 (90%-100%) |
| Crohn's Disease | 2 F | ≈2 g to ≈4 g | 2 (50%-60%) |
| colitis | 3 F; 1 M | ≈2 g to ≈8 g | 2 (less than 50%) |
|  |  |  | 1 (50%-60%) |
|  |  |  | 1 (70%-80%) |
| IBS | 28 F; 3 M | ≈2 g to ≈10 g | 10 (less than 50%) |
|  |  |  | 5 (50%-60%) |
|  |  |  | 10 (70%-80%) |
|  |  |  | 6 (90%-100%) |
| interstitial cystitis | 2 F; 1 M | ≈2 g to ≈10 g | 3 (70%-80%) |
| acne | 3 F | ≈4 g to ≈8 g | 1 (50%-60%) |
|  |  |  | 2 (70%-80%) |
| sinusitis | 4 F; 2 M | ≈2 g to ≈10 g | 1 (less than 50%) |
|  |  |  | 1 (50%-60%) |
|  |  |  | 2 (70%-80%) |
|  |  |  | 1 (90%-100%) |
| rheumatoid arthritis | 3 F; 1 M | ≈2 g to ≈4 g | 4 (90%-100%) |
| chronic fatigue | 13 F; 2 M | ≈2 g to ≈10 g | 1 (less than 50%) |
|  |  |  | 2 (70%-80%) |
|  |  |  | 12 (90%-100%) |
| asthma | 3 F; 1 M | ≈2 g to ≈8 g | 4 (90%-100%) |
| ADD | 4 F; 4 M | ≈4 g to ≈8 g | 1 (50%-60%) |
|  |  |  | 2 (70%-80%) |
|  |  |  | 1 (90%-100%) |
| rosacea | 5 F | ≈2 g to ≈8 g | 1 (less than 50%) |
|  |  |  | 1 (50%-60%) |
|  |  |  | 2 (70%-80%) |
|  |  |  | 1 (90%-100%) |

It is noted that the administration schedule and dosage varied from patient to patient depending on the severity of the disease state or physiological condition and as such, it was not possible to correlate the percent improvement to the amount of composition taken or the length of time the composition was taken. The data show that the effective amelioration of the disease state or physiological condition is completely unrelated to the age or gender of the patient (with the exception of patients less than six years of age).

Referring to Table 1, it can be seen that the composition of the present invention effectively treated various disease states and physiological conditions, including, but not limited to, autism, delayed development, acid reflux disease, impaired hearing, chronic ear infections, seasonal allergies, Fibromyalgia syndrome, Crohn's disease, colitis, irritable bowel syndrome, interstitial cystitis, acne, sinusitis, rheumatoid arthritis, chronic fatigue syndrome, asthma, attention deficit disorder, and rosacea.

EXAMPLE 27

A survey was made of persons using Composition A. The survey identified the responses of 111 test subjects who suffered from one of the disease states or adverse physiological conditions listed in Table 2 (irritable bowel syndrome, arthritis, fibromyalgia, hyperglycemia, hearing impairment, chronic fatigue, colitis, vaginal yeast infections, attention deficit disorder, sinusitis, seasonal allergies, acid reflux, multiple sclerosis, asthma, acne, autism, eczema and rosacea).

As set out in Table 2, the respondents are identified as male or female subjects, and the dosage administered to them daily is identified as grams of Composition A.

As shown in Table 2, percent improvements of the disease states or adverse physiological conditions were identified by the respondents, on a scale of 0 to 100%, with the percent improvement being set out in parenthesis following an identification of the number of individuals who reported that percent improvement in the test group.

For example, 11 subjects, including 9 females and 2 males, who were afflicted with irritable bowel syndrome, were administered 1.5 to 6 grams of Composition A daily, with continued daily administration for at least four months.

One subject in the 11-person test group reported 25% improvement, one subject reported 40% improvement, two subjects reported 50% improvement, three subjects reported 75% improvement, one subject reported 80% improvement, two subjects reported 90% improvement and one subject reported 95% improvement, in relation to the severity of the disease state or adverse physiological condition that was originally identified by persons in the test group as afflicting them.

The reported survey data of the test subjects set out in Table 2 evidence the efficacy of Composition A taken by such test subjects, in improving their condition of suffering from a specific disease state or adverse physiological condition (irritable bowel syndrome, arthritis, fibromyalgia, hyperglycemia, hearing impairment, chronic fatigue, colitis, vaginal yeast infections, attention deficit disorder, sinusitis, seasonal allergies, acid reflux, multisclerosis, asthma, acne, autism, eczema or rosacea), as specified in such Table 2.

TABLE 2

| Disease State/ Adverse Physiological Condition | # of Respondents (Male or Female) | Dosage Administered/ day | Percent Improvement |
| --- | --- | --- | --- |
| Irritable Bowel Syndrome | 9 F; 2 M | 1.5 g to 6 g | 1 (25%) |
|  |  |  | 1 (40%) |
|  |  |  | 2 (50%) |
|  |  |  | 3 (75%) |
|  |  |  | 1 (80%) |
|  |  |  | 2 (90%) |
|  |  |  | 1 (95%) |
| Arthritis | 1 F | 1.5 g | 1 (90%) |
| Fibromyalgia | 5 F; 3 M | 1.5 g to 6 g | 1 (40%) |
|  |  |  | 1 (75%) |
|  |  |  | 2 (80%) |
|  |  |  | 2 (90%) |
|  |  |  | 2 (100%) |
| Hyperglycemia | 1 M | 6 g | 1 (100%) |
| Hearing Impairment | 1 F; 1 M | 4.5 g to 6 g | 1 (90%) |
|  |  |  | 1 (80%) |
| Chronic Fatigue | 2 M; 16 F | 1.5 g to 7.5 g | 2 (25%) |
|  |  |  | 1 (40%) |
|  |  |  | 1 (50%) |
|  |  |  | 1 (60%) |
|  |  |  | 1 (70%) |
|  |  |  | 1 (75%) |
|  |  |  | 3 (80%) |
|  |  |  | 5 (90%) |
|  |  |  | 3 (100%) |
| Colitis | 1 F; 2 M | 3 g to 4.5 g | 1 (40%) |
|  |  |  | 1 (50%) |
|  |  |  | 1 (80%) |
| Vaginal Yeast Infections | 19 F | 3 g to 7.5 g | 1 (25%) |
|  |  |  | 1 (50%) |
|  |  |  | 2 (80%) |
|  |  |  | 1 (85%) |
|  |  |  | 2 (90%) |
|  |  |  | 2 (100%) |
| Attention Deficit Disorder | 2 F; 1 M | 1.5 g to 6 g | 1 (25%) |
|  |  |  | 1 (80%) |
|  |  |  | 1 (90%) |
| Sinusitis | 3 F; 1 M | 1.5 g to 6 g | 1 (25%) |
|  |  |  | 1 (75%) |
|  |  |  | 2 (90%) |
| Seasonal Allergies | 2 F | 3 g to 6 g | 2 (90%) |
| Acid Reflux | 4 F; 3 M | 1.5 g to 3 g | 1 (25%) |
|  |  |  | 2 (50%) |
|  |  |  | 2 (90%) |
|  |  |  | 2 (100%) |
| Multiple Sclerosis | 1 M | 3 g | 1 (25%) |
| Asthma | 1 F | 6 g | 1 (100%) |
| Acne | 2 F | 3 g to 6 g | 2 (75%) |
| Acid Reflux | 2 F | 1.5 g | 1 (70%) |
|  |  |  | 1 (80%) |
| Arthritis | 1 F | 7.5 g | 1 (100%) |
| Autism | 3 F; 16 M | 3 g to 7.5 g | 1 (20%) |
|  |  |  | 1 (30%) |
|  |  |  | 4 (50%) |
|  |  |  | 3 (60%) |
|  |  |  | 4 (70%) |
|  |  |  | 3 (80%) |
|  |  |  | 2 (90%) |
|  |  |  | 1 (100%) |
| Eczema | 4 F; 1 M | 1.5 g to 6 g | 1 (60%) |
|  |  |  | 1 (70%) |
|  |  |  | 3 (90%) |
| Rosacea | 1 M | 3 g | 1 (95%) |

While the invention has been described herein with reference to various specific embodiments, it will be appreciated that the invention is not thus limited, and extends to and encompasses various other modifications and embodiments, as will be appreciated by those ordinarily skilled in the art. Accordingly, the invention is intended to be broadly construed and interpreted, in accordance with the ensuing claims.

What is claimed is:

1. A probiotic composition, consisting of 100 million colony forming units (CFUs) of *Bacillus subtilis,* 200 million CFUs of *Bacillus coagulans,* 100 million CFUs of *Enterococcus faecium*, and a carrier medium consisting of fructo-oligosaccharides.

2. The probiotic composition of claim 1, wherein all ingredients are in dry powder form.

3. A probiotic composition dose form, consisting of a gelatin capsule and a probiotic composition contained in said capsule, wherein said probiotic composition consists of 100 million colony forming units (CFUs) of *Bacillus subtilis,* 200 million CFUs of *Bacillus coagulans,* 100 million CFUs of *Enterococcus faecium*, and fructo-oligosaccharides, and said capsule is devoid of any enteric coating.

* * * * *